US011246675B2

(12) United States Patent
Menut et al.

(10) Patent No.: US 11,246,675 B2
(45) Date of Patent: Feb. 15, 2022

(54) SURGICAL C-SECTION DRAPE WITH TUNNEL

(71) Applicant: Medline Industries, LP, Northfield, IL (US)

(72) Inventors: Matthieu Menut, Nantes (FR); Cvetanka Gjurovska, Arnhem (NL); Sabrina Nael-Pitre, St. Julie de Vouvantes (FR)

(73) Assignee: Medline Industries, LP, Northfield, IL (US)

( * ) Notice: Subject to any disclaimer, the term of this patent is extended or adjusted under 35 U.S.C. 154(b) by 329 days.

(21) Appl. No.: 15/874,417

(22) Filed: Jan. 18, 2018

(65) Prior Publication Data

US 2019/0216565 A1    Jul. 18, 2019

(51) Int. Cl.
*A61B 46/00* (2016.01)
*A61B 46/20* (2016.01)
(Continued)

(52) U.S. Cl.
CPC .............. *A61B 46/20* (2016.02); *A61B 46/30* (2016.02); *A61B 46/40* (2016.02);
(Continued)

(58) Field of Classification Search
CPC ......... A61B 46/00; A61B 46/20; A61B 46/30; A61B 2046/236; A61B 2046/205;
(Continued)

(56) References Cited

U.S. PATENT DOCUMENTS 3,667,458 A    6/1972 Krebs
3,698,395 A    10/1972 Hasson
(Continued)

FOREIGN PATENT DOCUMENTS

CN    201602900 U    10/2010
CN    201602902        10/2010
(Continued)

OTHER PUBLICATIONS

European Extended Search Report for European Application No. 18200143 dated Mar. 29, 2019.
(Continued)

*Primary Examiner* — Rachael E Bredefeld
*Assistant Examiner* — Brant T Bennett
(74) *Attorney, Agent, or Firm* — Fitch, Even, Tabin & Flannery LLP

(57) ABSTRACT

Disclosed is a surgical drape configured to selectively allow or block a patient's view of a surgical field, as is desired particularly in Caesarean section operations. Generally, the surgical drape includes a mainsheet and a screen connected to the mainsheet. The mainsheet is equipped with a surgical fenestration and the screen is equipped with a screen fenestration and a flexible tunnel material forming a tunnel between a surgeon-facing side of the screen and a patient-facing side of the screen. The drape is equipped with at least one flap that covers the screen fenestration during the surgical procedure. Upon birth, the infant is passed through the tunnel to greet the mother, and a flap is then closed to cover the screen fenestration.

20 Claims, 11 Drawing Sheets

(51) Int. Cl.
 *A61B 17/00* (2006.01)
 *A61B 46/23* (2016.01)
(52) U.S. Cl.
 CPC .............. *A61B 2017/00902* (2013.01); *A61B 2046/205* (2016.02); *A61B 2046/236* (2016.02)
(58) Field of Classification Search
 CPC ..... A61B 2046/201; A61F 2013/15073; A61F 13/15; A61F 2013/00089; A61G 13/10; A61G 13/102; A61G 10/005
 USPC ........................................ 128/853, 854, 856
 See application file for complete search history.

(56) References Cited

U.S. PATENT DOCUMENTS

| | | |
|---|---|---|
| 3,707,964 A | 1/1973 | Collins |
| 3,721,242 A | 3/1973 | Krusko |
| 3,750,664 A | 8/1973 | Collins |
| 3,763,857 A | 10/1973 | Schrading |
| 3,791,381 A | 2/1974 | Krzewinski |
| 3,799,161 A | 3/1974 | Collins |
| 3,826,253 A | 7/1974 | Larsh |
| 4,089,331 A | 5/1978 | Hartigan |
| 4,169,472 A | 10/1979 | Morris |
| 4,192,312 A | 3/1980 | Wilson |
| 4,205,668 A | 6/1980 | Criddle |
| D256,161 S | 7/1980 | Oliver |
| 4,384,573 A | 5/1983 | Elliott |
| 4,489,720 A | 12/1984 | Morris |
| 4,559,937 A | 12/1985 | Vinson |
| 4,586,498 A | 5/1986 | Morris |
| 4,616,642 A | 10/1986 | Martin |
| 4,798,201 A | 1/1989 | Rawlings |
| 4,869,271 A | 9/1989 | Idris |
| 4,890,628 A | 1/1990 | Jackson |
| 4,899,762 A | 2/1990 | Muller |
| 4,944,737 A | 7/1990 | Bloom |
| 5,042,507 A | 8/1991 | Dowdy |
| 5,060,662 A | 10/1991 | Farnswoth |
| 5,195,893 A | 3/1993 | Casale |
| 5,197,493 A | 3/1993 | Grier-Idris |
| 5,209,243 A * | 5/1993 | Glassman .............. A61B 46/00 128/849 |
| 5,345,946 A | 9/1994 | Butterworth |
| 5,380,278 A | 1/1995 | Mombrinie |
| 5,464,024 A | 11/1995 | Mills |
| D373,921 S | 9/1996 | Palomo |
| 5,778,889 A | 7/1998 | Jascomb |
| 5,778,890 A | 7/1998 | Lofgren |
| 5,800,483 A | 9/1998 | Vought |
| 5,803,086 A | 9/1998 | Scholz |
| 5,860,420 A | 1/1999 | Wiedner |
| 5,875,780 A | 3/1999 | Rodriguez |
| D408,533 S | 4/1999 | Niedospial, Jr |
| 5,991,666 A | 11/1999 | Vought |
| 6,007,564 A | 12/1999 | Haverstock |
| 6,019,102 A | 2/2000 | Becker |
| 6,032,670 A | 3/2000 | Miller |
| 6,199,553 B1 | 3/2001 | Hafer |
| 6,213,124 B1 | 4/2001 | Butterworth |
| 6,314,958 B1 | 11/2001 | Harroll |
| 6,345,621 B1 | 2/2002 | Chandler |
| D467,345 S | 12/2002 | Gingles |
| 6,497,233 B1 | 12/2002 | DeAngelis |
| 6,612,310 B2 | 9/2003 | Sklar |
| 6,694,981 B2 | 2/2004 | Gingles |
| 6,725,864 B2 | 4/2004 | Ewonce |
| 6,835,256 B2 | 12/2004 | Menzies |
| 6,843,252 B2 | 1/2005 | Harrison |
| 6,923,186 B2 | 8/2005 | Gavette |
| 6,966,320 B1 | 11/2005 | Baynes |
| 7,044,132 B2 * | 5/2006 | Masini .................. A61B 46/00 128/849 |
| 7,059,371 B2 | 6/2006 | Renn |
| 7,086,404 B2 | 8/2006 | Dusenbery |
| D539,904 S | 4/2007 | Inoue |
| D541,414 S | 4/2007 | Wallace |
| 7,588,034 B2 | 9/2009 | Mathis |
| D615,646 S | 5/2010 | Russell |
| 7,752,768 B2 | 7/2010 | Young |
| 7,853,311 B1 | 12/2010 | Webb |
| D637,296 S | 5/2011 | Matthews |
| 8,011,371 B2 | 9/2011 | Rotolo |
| 8,079,365 B2 | 12/2011 | Block |
| D653,330 S | 1/2012 | Ecabert |
| D653,331 S | 1/2012 | Ecabert |
| D653,333 S | 1/2012 | Ecabert |
| D653,751 S | 2/2012 | Ecabert |
| D653,752 S | 2/2012 | Pittet |
| D653,753 S | 2/2012 | Ecabert |
| 8,459,265 B2 | 6/2013 | Young |
| D693,603 S | 11/2013 | Esquivel |
| 8,721,629 B2 | 5/2014 | Hardman |
| 8,783,262 B2 | 7/2014 | Carrez |
| 8,967,150 B2 | 3/2015 | Carrez |
| D739,012 S | 9/2015 | Hanuka |
| 9,278,166 B2 | 3/2016 | Czajka, Jr |
| D796,685 S | 9/2017 | Ohizep |
| D838,375 S | 1/2019 | Cashin |
| D839,440 S | 1/2019 | Cashin |
| 10,188,474 B2 * | 1/2019 | Jarrelle ................. A61B 46/00 |
| D851,772 S | 6/2019 | Haines |
| 2001/0023697 A1 | 9/2001 | Hinley |
| 2002/0174870 A1 | 11/2002 | Ewonce |
| 2003/0051362 A1 | 3/2003 | Buckman |
| 2003/0159966 A1 | 8/2003 | McMichael |
| 2003/0187458 A1 | 10/2003 | Carlson |
| 2003/0205233 A1 * | 11/2003 | Aboul-Hosn .......... A61B 46/23 128/849 |
| 2004/0103903 A1 | 6/2004 | Falahee |
| 2004/0118049 A1 | 6/2004 | Chen |
| 2004/0118409 A1 | 6/2004 | Griesbach |
| 2005/0234322 A1 | 10/2005 | Lober |
| 2006/0169290 A1 | 8/2006 | Harris |
| 2006/0201521 A1 | 9/2006 | Masini |
| 2006/0207609 A1 | 9/2006 | Gil |
| 2006/0219249 A1 | 10/2006 | Czajka |
| 2008/0006279 A1 | 1/2008 | Bodenham |
| 2009/0158487 A1 | 6/2009 | Paulsen |
| 2009/0277460 A1 | 11/2009 | Carrez |
| 2010/0192960 A1 | 8/2010 | Rotolo |
| 2010/0263678 A1 | 10/2010 | Baumann |
| 2011/0015557 A1 | 1/2011 | Aali |
| 2011/0030702 A1 | 2/2011 | Czajka |
| 2011/0041995 A1 | 2/2011 | Adams |
| 2011/0126845 A1 | 6/2011 | Hoffmann |
| 2011/0214679 A1 | 9/2011 | Chua |
| 2011/0247634 A1 | 10/2011 | Young |
| 2012/0017921 A1 | 1/2012 | Esquivel |
| 2012/0222686 A1 | 9/2012 | Lockwood |
| 2012/0222687 A1 | 9/2012 | Czajka |
| 2012/0298115 A1 | 11/2012 | Haines |
| 2013/0284187 A1 | 10/2013 | Esquivel |
| 2013/0304080 A1 | 11/2013 | Landry |
| 2013/0312770 A1 | 11/2013 | Young |
| 2014/0012119 A1 | 1/2014 | Geaghan |
| 2014/0261457 A1 | 9/2014 | Lother |
| 2015/0135398 A1 | 5/2015 | Czajka |
| 2015/0359596 A1 | 12/2015 | Jarrelle |
| 2016/0135915 A1 | 5/2016 | Czajka, Jr |
| 2017/0258543 A1 | 9/2017 | Chua |

FOREIGN PATENT DOCUMENTS

| | | |
|---|---|---|
| CN | 101496742 | 3/2011 |
| CN | 102470019 | 5/2012 |
| EP | 2151211 | 2/2010 |
| SU | 445412 | 10/1974 |
| WO | 9510986 | 4/1995 |
| WO | 2006094062 | 9/2006 |
| WO | 2011088326 | 7/2011 |
| WO | 2012078620 | 6/2012 |
| WO | 2012161869 | 11/2012 |

(56) References Cited

FOREIGN PATENT DOCUMENTS

| WO | 2013036387 | 3/2013 |
|---|---|---|
| WO | 2014083573 | 6/2014 |
| WO | 2015191953 | 12/2015 |

OTHER PUBLICATIONS

Medline Cesarean Section Surgical Drape with Pouch and Fenestration. No date specified. https://www.medline.com/product/Cesarean-Section-Surgical-Drape-with-Pouch-and-Fenestration/Z05-PF07160 (Year: 0).
Australian Patent Application No. 2012223335; Patent Examination Report No. 1; dated Aug. 14, 2015; 4 pages.
Canadian Patent Application No. 2,832,104; Office Action dated Aug. 12, 2015; 5 pages.
Chinese Patent Application No. 2012800215110; Office Action dated Mar. 20, 2015 with English translation.
Extended European Search Report from European Application No. 12751757.1 dated Aug. 12, 2014.
International Search Report and Written Opinion; PCT Patent Application No. PCT/US2014/023215; dated Jul. 24, 2014.
Notification of the First Office Action dated Mar. 20, 2015 from Chinese Patent Application No. 2012800215110.
PCT, Notification Concerning Transmittal of International Preliminary Report on Patentability, in International Application No. PCT/US2012/27284, dated Sep. 12, 2013.
PCT, Notification of Transmittal of the International Search Report and the Written Opinion of the International Searching Authority, or the Declaration, in International Application No. PCT/US12/27284, dated Jun. 29, 2012.
Chinese Patent Application No. 2012800215110; Office Action dated Nov. 4, 2015 with English translation.
Article 94(3) EPC from European Patent Application No. 12751757.1 dated Jan. 5, 2017; 7 pages.
Australian Patent Application No. 2012223335; Patent Examination Report No. 2; dated Aug. 15, 2016; 6 pages.
International Search Report and Written Opinion from PCT/US2017/022278 dated Jun. 19, 2017; 11 pages.
International Search Report and Written Opinion from PCT/US2017/022450 dated Jun. 7, 2017; 12 pages.
Extended European Search Report from European Patent Application No. 17173255.5 dated Aug. 18, 2017; 10 pages.
European Supplementary Search Report for European Application No. 17767321, dated Oct. 18, 2019.
Australian Patent Application No. 2019200113; Patent Examination Report No. 1; dated May 10, 2019; 6 pages.
Chinese Office Action from corresponding Chinese Patent Application No. 201780017592.X dated Jul. 8, 2020 with English Translation; 22 pages.
Chinese Office Action with English translation from corresponding Chinese Patent Application No. 201780017592.X dated Jan. 27, 2021; 25 pages.

\* cited by examiner

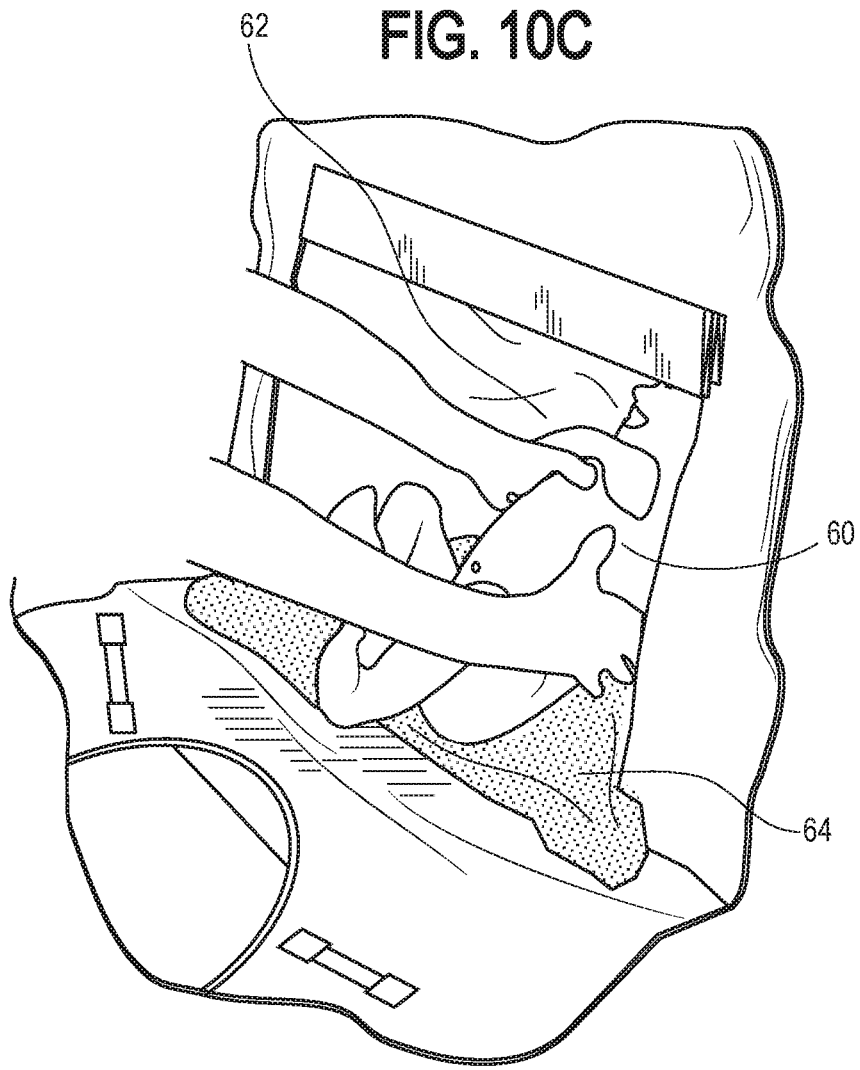

SURGICAL C-SECTION DRAPE WITH TUNNEL

TECHNICAL FIELD

The present application relates to a drape for covering a patient during a surgical procedure.

BACKGROUND

Currently, a traditional Cesarean section procedure, also known as "C-section," is most commonly performed with the patient covered by a solid surgical drape. The drape is typically constructed of a multi-layer combination of spunbond and meltblown materials, as well as impervious films, commonly referred to as SMS nonwoven fabric, or bilaminated and trilaminated impervious and absorbent materials.

Because the mother is typically awake and alert during the C-section, it is desirable to provide a barrier or screen to occlude the mother's view of the surgical area during the procedure. Many traditional drapes are in a "T" shape, with the top portion of the "T" acting as the anesthesia screen that obscures the patient's view of the surgical area. The drape is placed over the patient to isolate a sterile field near the patient's abdomen. The anesthesia screen is propped up on vertical standards at each side of the operating table near the patient's head or on a crossbar proximal the head.

In this arrangement, the mother does not have an opportunity to see her newborn immediately after delivery. It is desirable in the first moments after birth for the mother and child to establish an immediate connection. It is especially desirable for the infant and mother to maintain skin-to-skin contact immediately after birth. Such maintenance of skin-to-skin contact is believed to provide a number of benefit for both the mother and the newborn infant. Because traditional surgical drapes obscure the mother's view of the newborn in the first moments after delivery, the mother and child do not have an opportunity to establish an immediate physical connection.

To address this concern, it is known to provide surgical drapes that incorporates a coverable window and an opaque flap that can be attached and detached to alternately obscure and expose the window. It has now been realized that many such known drapes are undesirable in that they are configured in ways that might allow for contamination of the surgical field once the flap is removed, particularly if the flap is folded into the surgical field.

A new surgical drape has now been devised. Generally, the drape includes a mainsheet having a mainsheet fenestration through which the Caesarean section procedure may be performed, the mainsheet having various edges and portions including a head-oriented edge. The drape further includes a screen attached to the mainsheet at the head-oriented edge, the screen including a screen fenestration and at least one flap that covers the screen fenestration during the surgical procedure. Preferably, the screen includes at least two flaps, one disposed on the patient-side of the screen and the other disposed on the surgeon-side of the screen. Each flap is substantially opaque to thereby inhibit the patient's visual access through the screen fenestration. The screen is further equipped with a flexible tunnel material that is configured to form a tunnel extending from the surgeon-side to the patient-side, the tunnel generally extending in the direction of the patient. In use, the surgeon-side flap may originally be supplied in an occluding position while the patient-side flap may be disposed in an open position. Upon performance of the surgery and extraction of the newborn infant, the surgeon-side flap may be lifted and secured into an open position, whereupon the infant is passed through the tunnel to greet the mother. At this point the patient-side flap is closed and secured, and optionally the surgeon-side flap likewise may be re-closed. In this manner, the mother may view the birth of the infant, or may view the infant immediately after birth, and may establish skin-to-skin contact as quickly as possible.

BRIEF DESCRIPTION OF THE DRAWINGS

FIGS. 10A-E illustrate sequentially the passage of a newborn infant through the tunnel and screen fenestration to greet the mother; FIGS. 10A-D illustrating the surgeon-facing side of the screen and FIG. 10E illustrating the patient-facing side of the screen.

DETAILED DESCRIPTION

Figure 1:
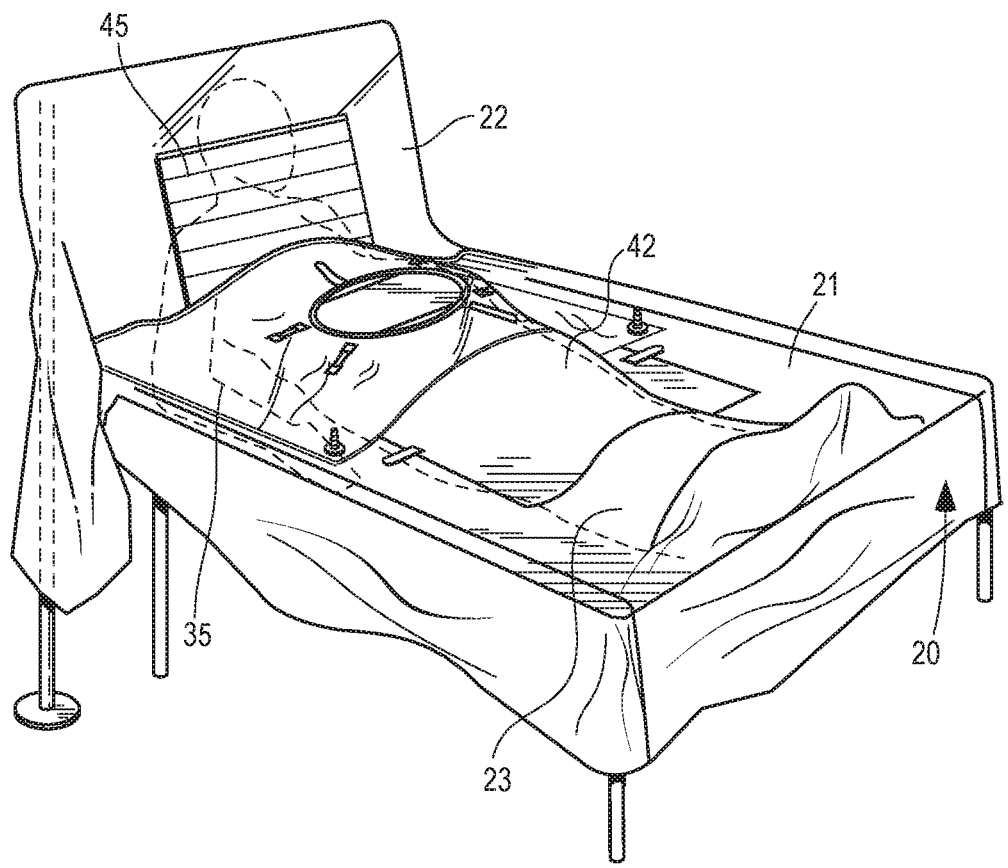
FIG. 1 is a perspective view of a surgical drape in accordance with one embodiment of the invention, shown in use positioned over a patient in a surgical bed.
Figure 2:
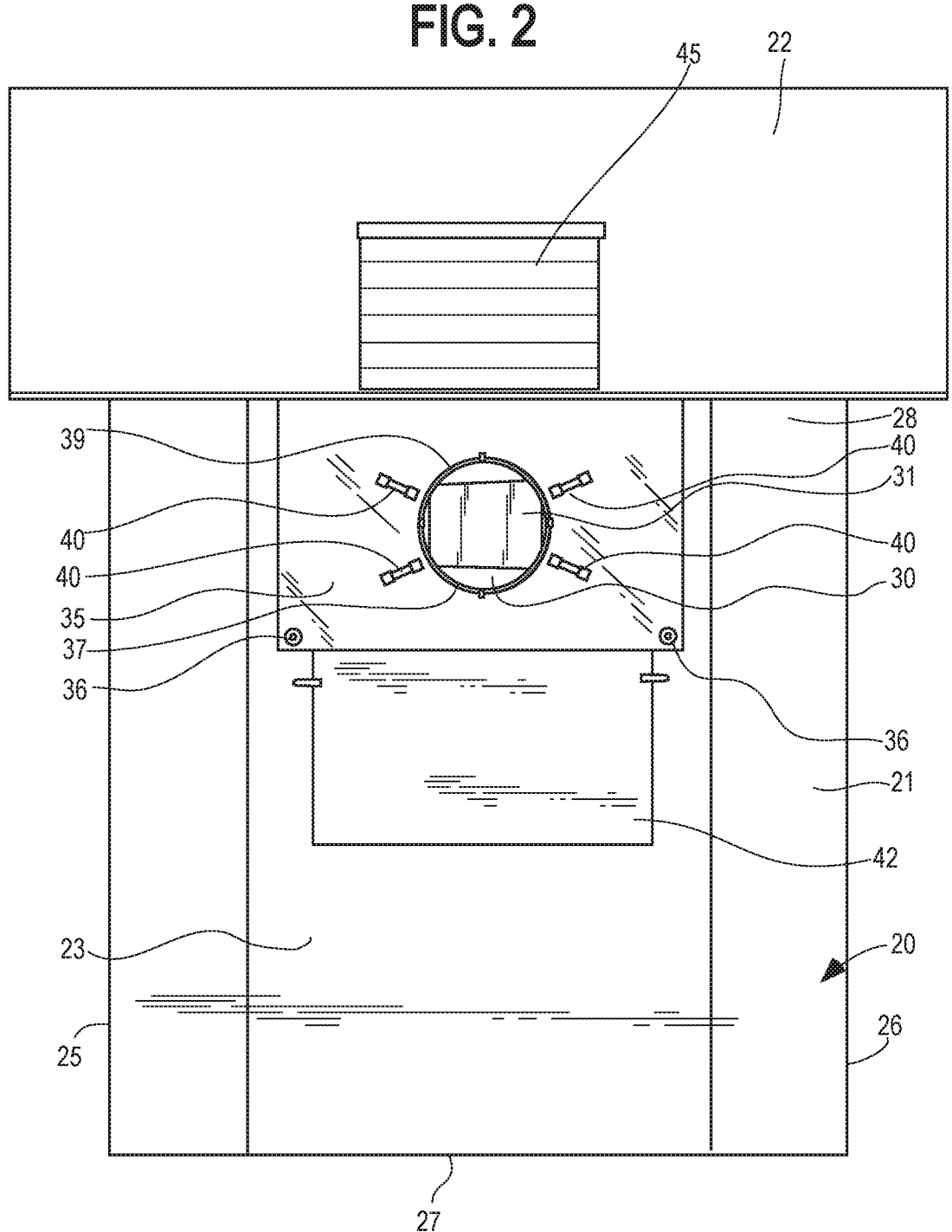
FIG. 2 is a top plan view of the surgical drape shown in FIG. 1.
Figure 3:
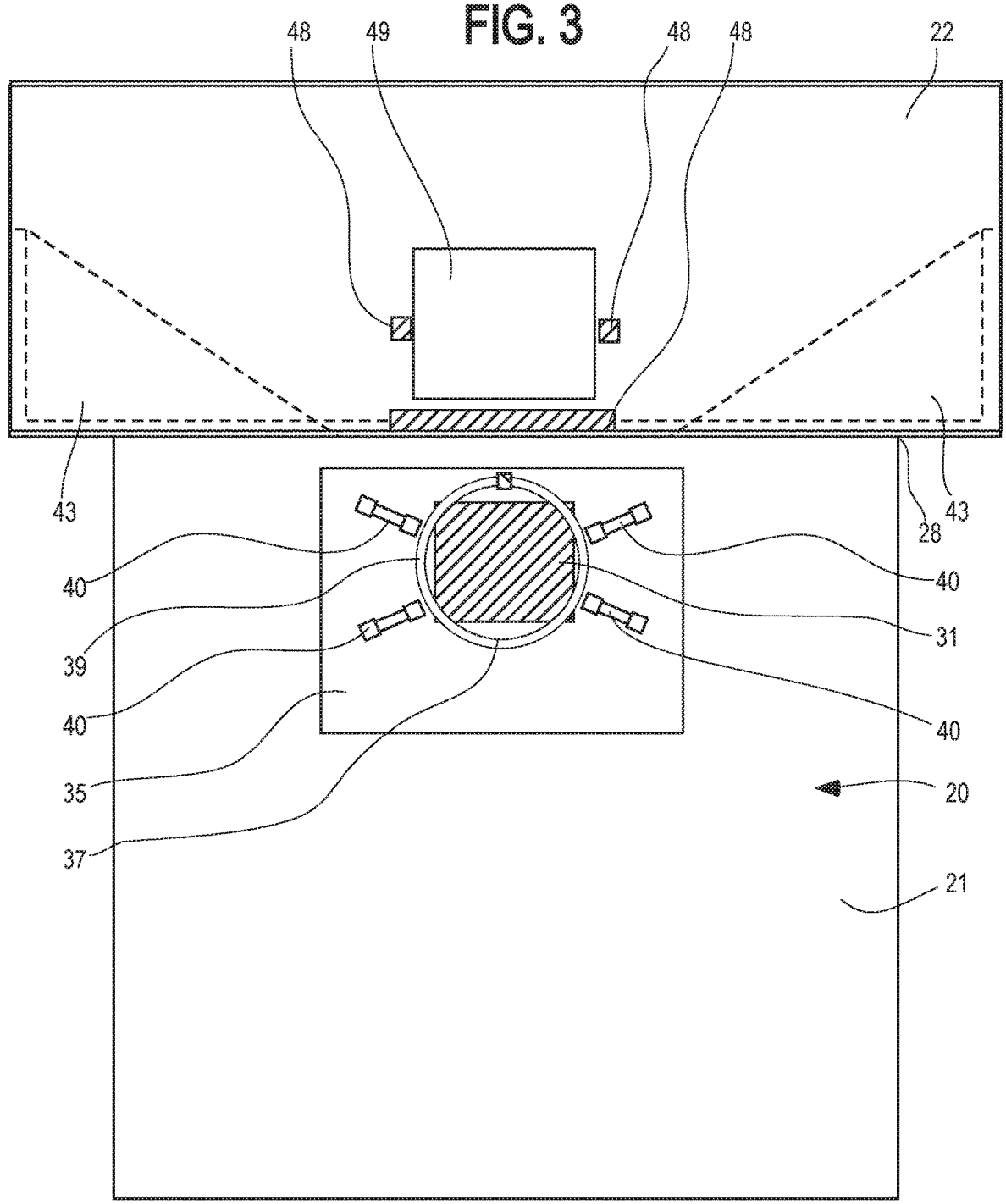
FIG. 3 is a top plan view of the surgical drape shown in FIG. 1 with the surgeon-side flap and optional absorbent pad removed.
Figure 4:
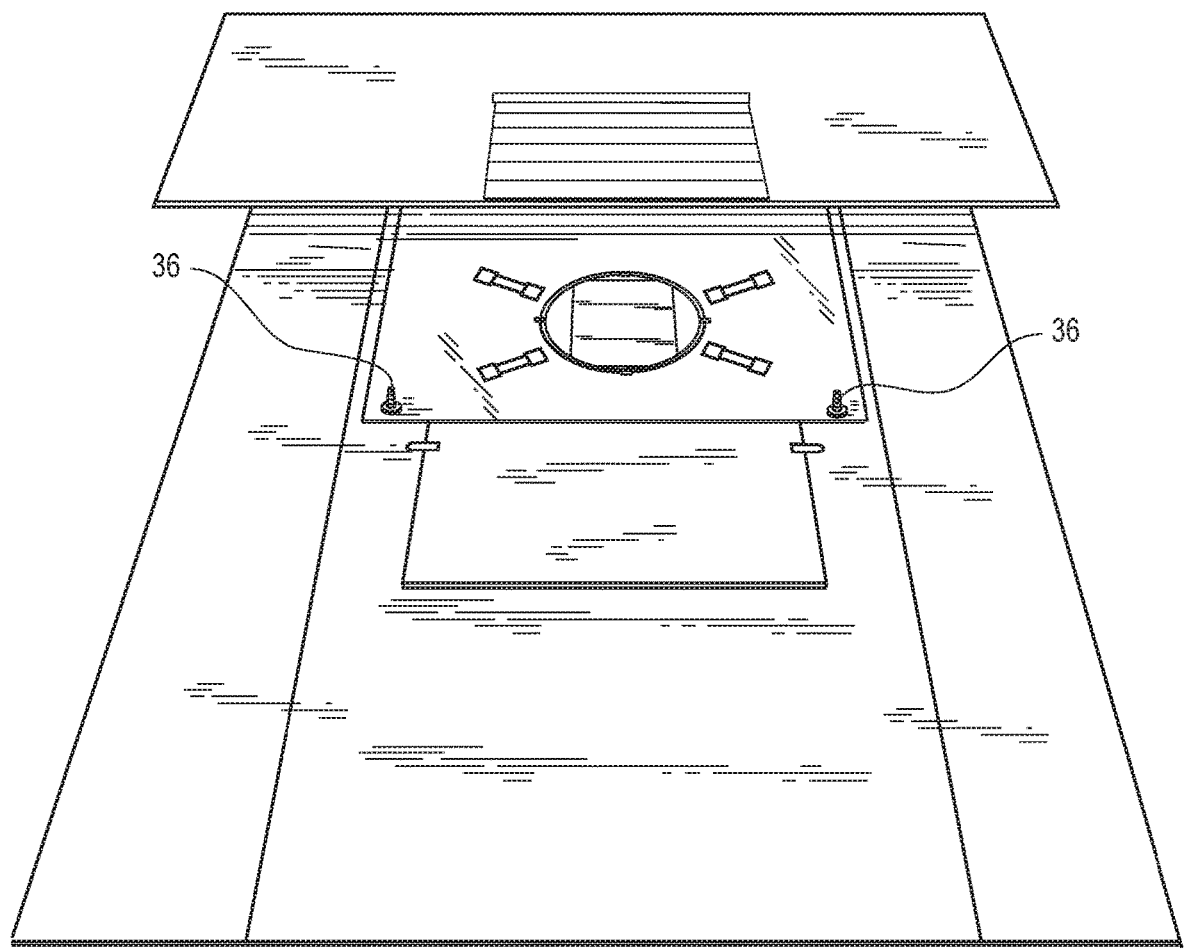
FIG. 4 is a front perspective view of the surgical drape shown in FIG. 1.
Figure 5:
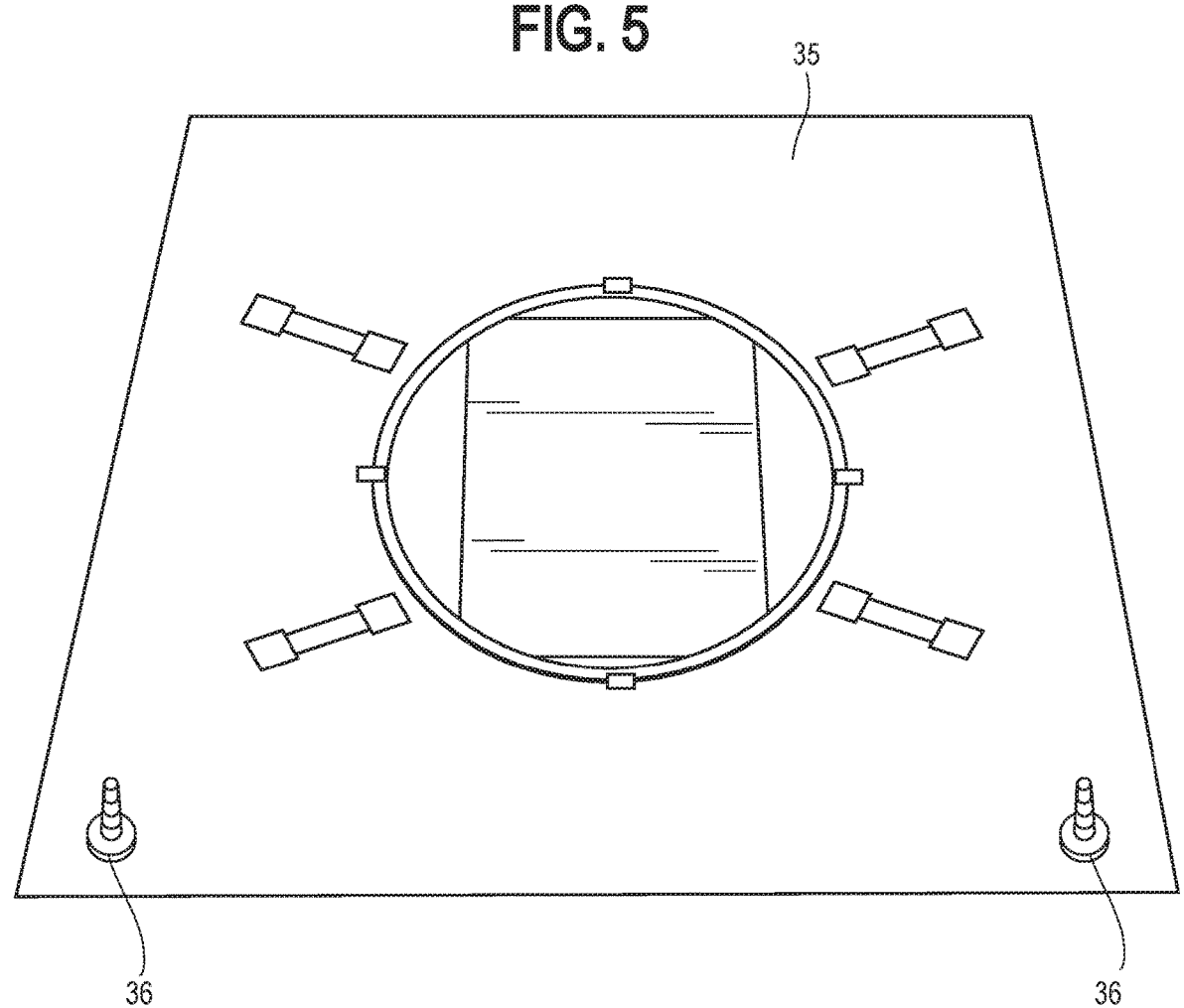
FIG. 5 is a perspective view of the mainsheet fenestration region of the mainsheet, illustrating the fluid-collecting pouch.
Figure 6:
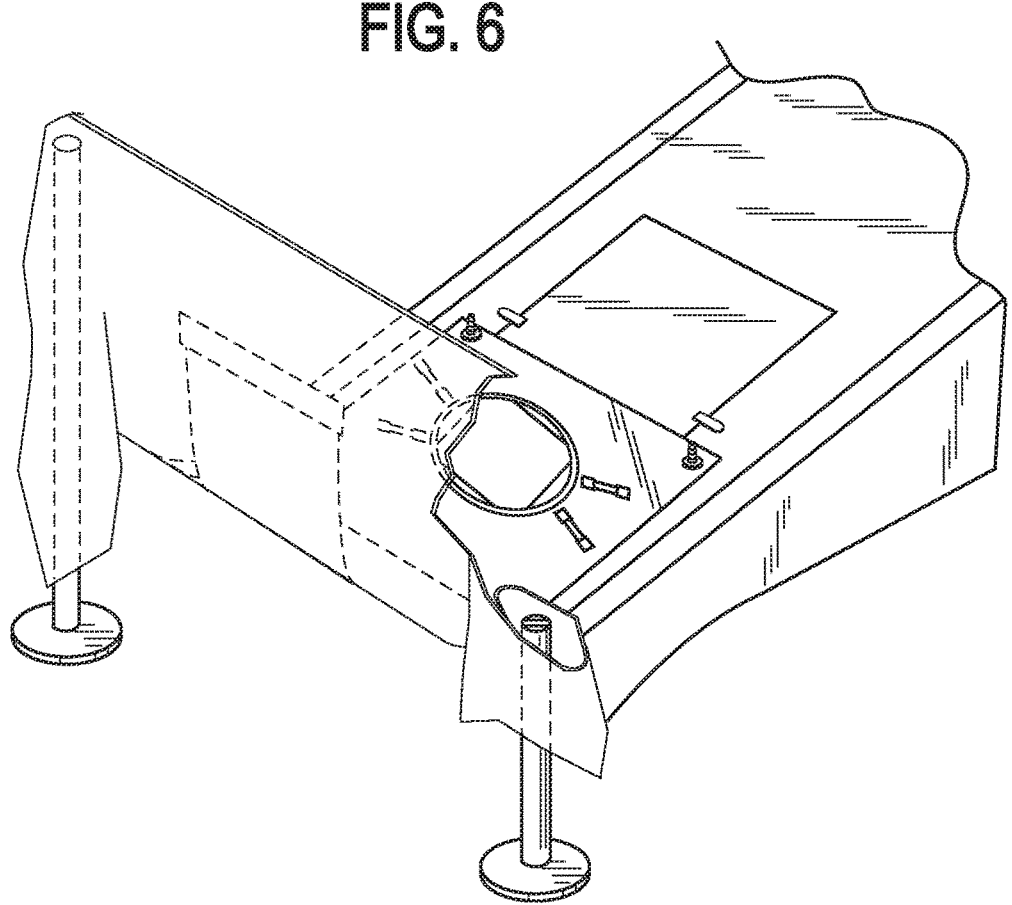
FIG. 6 is a rear perspective view, partially cut away, of the surgical drape and bed shown in FIG. 1.

Referring to FIGS. 1-3, the drape 20 includes generally a mainsheet 21 and a screen 22. With particular reference to FIG. 2, the mainsheet 21 includes a central portion 23, side edges 25, 26, a foot-oriented edge 27, and a head-oriented edge 28. As illustrated, the screen 22 is disposed at the head-oriented edge 28, and is preferably formed as a separate piece of material that is secured to the mainsheet 21 via adhesive. The mainsheet 21 includes a mainsheet fenestration 30 through which a surgery accessing a patient's body may be performed. The mainsheet fenestration 30 generally comprises an opening formed in the material of mainsheet 21, and is sized to allow sufficient access to a patient's abdominal region to perform a C-section procedure. The mainsheet fenestration 30 is covered with a flexible adhesive film known in the industry as "incise film," which may be formed from polyurethane or another suitable material, and a liner 31. In some embodiments, the mainsheet fenestration 30 may be completely covered with incise film to form a "full incise" fenestration. It is contemplated that a "fenestrated incise" structure (not shown) alternatively may be employed, wherein there is adhesive disposed around the perimeter of the mainsheet fenestration leaving an opening in a center portion of the flexible adhesive film through which the patient's skin is exposed to permit incisions to be made directly though the exposed skin.

When the surgical drape 20 is laid over a patient, the "full incise" film is first covered with a removable backing (not shown), as is conventional. Before the procedure is performed and after the surgical drape 20 is laid over the patient, the removable backing is removed, exposing the adhesive bottom surface of the incise film and causing the film to adhere to the skin of the patient. When the procedure is performed, incisions may be made directly through the flexible adhesive film.

The illustrated mainsheet fenestration 30 is substantially surrounded by an optional fluid collection pouch 35. The fluid collection pouch 35 is composed of a plastic material that is impervious to fluid. The fluid collection pouch 35 surrounds the mainsheet fenestration 30 in a sealing fashion such that any fluids released from the surgical site during the procedure will run off the sheet into fluid collection pouch 35. This prevents fluids from running off the mainsheet 21 and onto the floor or other areas where fluids are not desired. The fluid collection pouch 35 may include one or more suction ports 36 for connection to suction equipment for aspirating the fluids from the fluid collection pouch 35. The fluid collection pouch 35 may be secured to the mainsheet 31 via any suitable fashion, such as via double-sided adhesive tape.

The fluid collection pouch 35 includes an opening 37 through which the surgeon may access the mainsheet fenestration 30. The edges of the opening 37 may be bound by a formable material 39, such as a malleable wire encased in plastic. Such formable material 39 allows the surgeon to shape the opening of fluid collection pouch 35 to allow for easier access to fenestration 30 or to reconfigure the shape of fluid collection pouch 35 in a manner that is most effective for the particular procedure.

The illustrated mainsheet 21 includes malleable bars 40. The malleable bars 40 are composed of a malleable metal material and of a plastic material, and are present to enable the surgeon to adjust the shape of the fenestration to improve fluids collection. By bending upwardly, the surgeon can adjust the shape and elevation of the open fenestration.

The mainsheet 21 further may include one or more line retainers (not shown) for securing wires or lines to the surgical drape 20. Such line retainers include may be formed in any suitable fashion and may include two plies of hook and loop material that may be separated at one end, but attached at another end. When the plies of the hook and loop material are separated, a line may be inserted between the two plies, and when the plies are joined again, the hook and loop material captures the line between the plies. The tabs alternatively may be formed from tape or from other suitable material. Additionally, cord holding tabs (not shown) may be positioned near the head-oriented edge of the mainsheet.

The mainsheet 21 also may include an optional absorbent pad 42, which, as shown, is configured as a separate pad disposed on and secured to the mainsheet 21. The absorbent pad 42 is located near fenestration 30 and is composed of a material that is suitable for absorbing fluids that are generated during the surgical procedure. This absorbent pad 42 provides another measure of fluid retention in the instance where fluids are not collected by the fluid collection pouch 35. As shown in FIGS. 1 and 2, the drape 20 is further equipped with a surgeon-side flap 45, the purpose of which will be discussed below.

With particular reference to FIG. 3, the drape 20 may include optional armboard portions 43 (shown in hidden lines). The armboard portions are intended to cover armboard portions of a surgical bed or cot (not shown), and are composed of generally rectangular sheets of material that are secured to the mainsheet 21 and that are folded behind the mainsheet 21 when not in use. FIG. 3 further illustrates double-sided tape 48 that is useful in securing the surgeon-side flap 45 (not seen in FIG. 3) in a closed position with respect to the screen 22. As further illustrated, the screen 22 includes a screen fenestration 49, this screen fenestration 49 permitting passage of a newborn infant therethrough.

Figure 7:
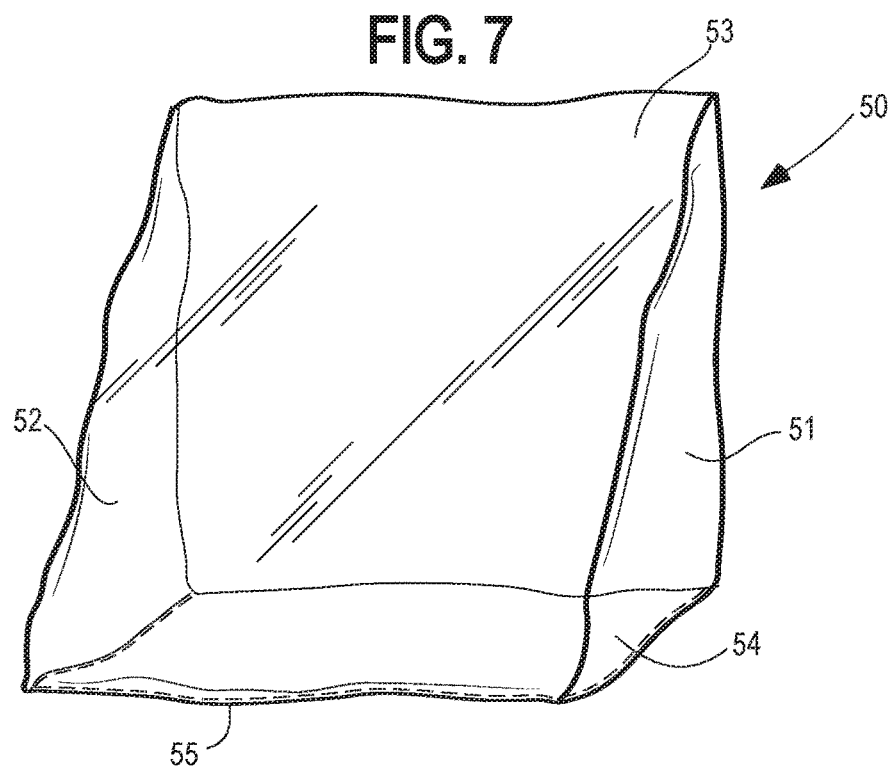
FIG. 7 is a perspective view of the tunnel-forming material that is secured on the patient-side of the screen to form an infant-transporting tunnel.

With reference now to FIG. 7, the tunnel material 50 is in the form of a transparent, flexible structure having generally triangular first side 51, second side 52, and front face 53, and bottom 54. The first and second sides 51, 52 and front face 53 are preferably secured to the bottom 54 via heat sealing or another suitable method, and perforations 55 optionally may be formed in the region of the sealed surfaces to form tear lines. This tunnel structure is secured to the patient-side of the screen 22 via adhesive or other suitable form of connection. When the surgical drape 20 is laid over a patient, or shortly thereafter, the perforations 20 may be torn to open the tunnel structure to form a tunnel connecting the surgeon-facing side and the patient-facing side of the screen 22.

Figure 8:
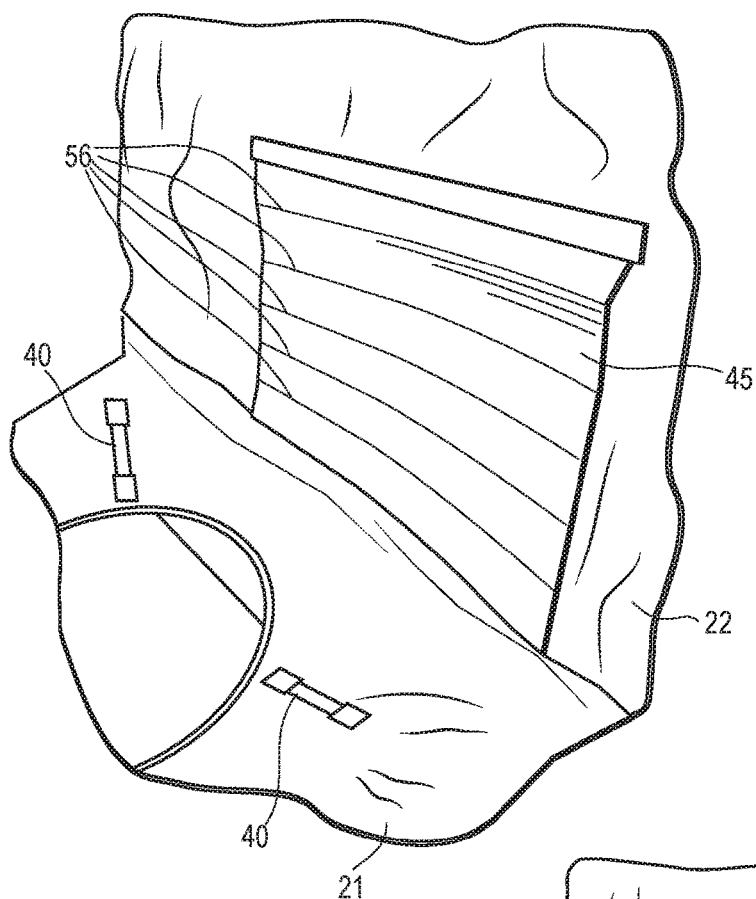
FIG. 8 is a perspective view illustrating the surgical drape in an operating position, showing the surgeon-side flap in a closed position.
Figure 9:
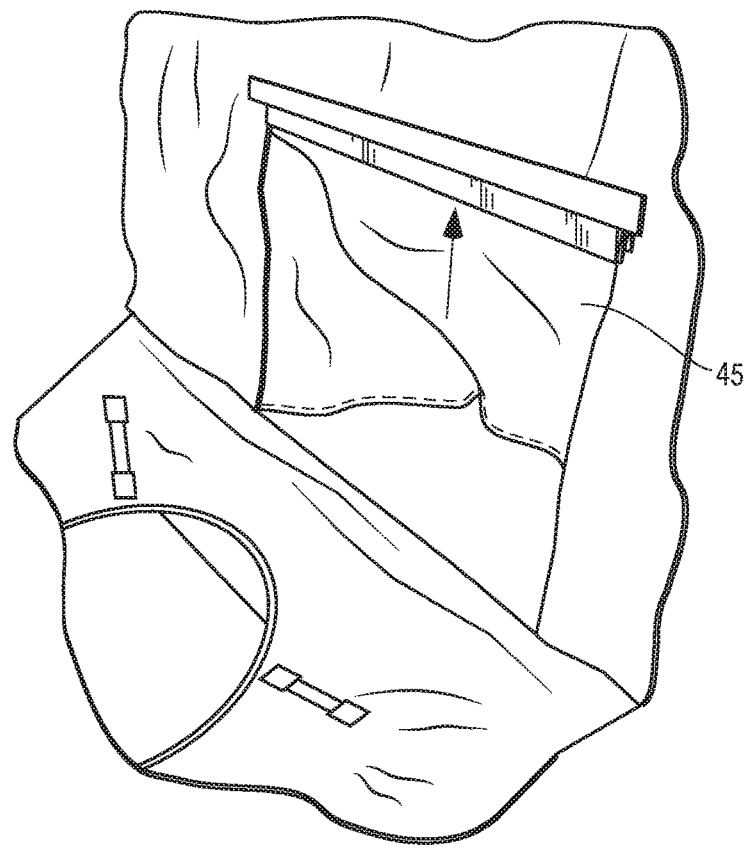
FIG. 9 is a view similar to FIG. 8 but showing the surgeon-side flap in an open, secured position.
Figure 10A:
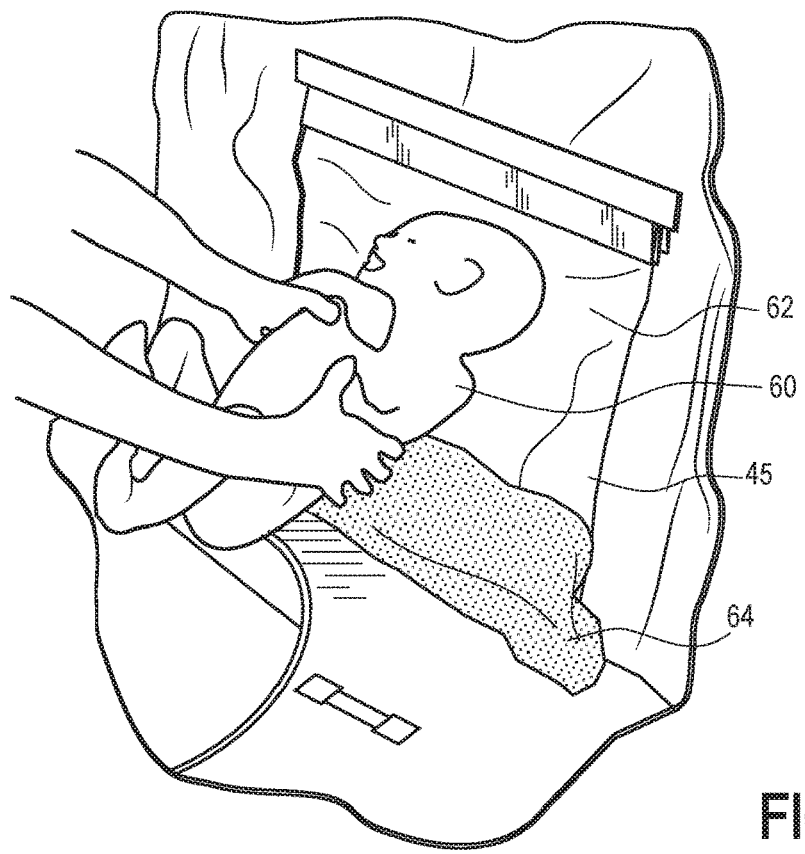
Figure 10B:
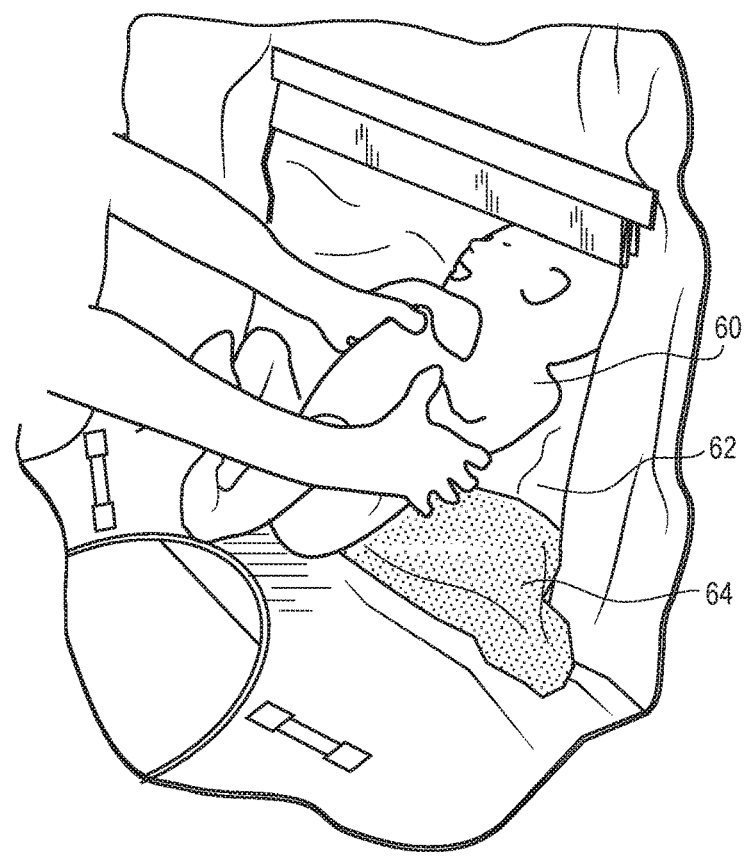
Figure 10D:
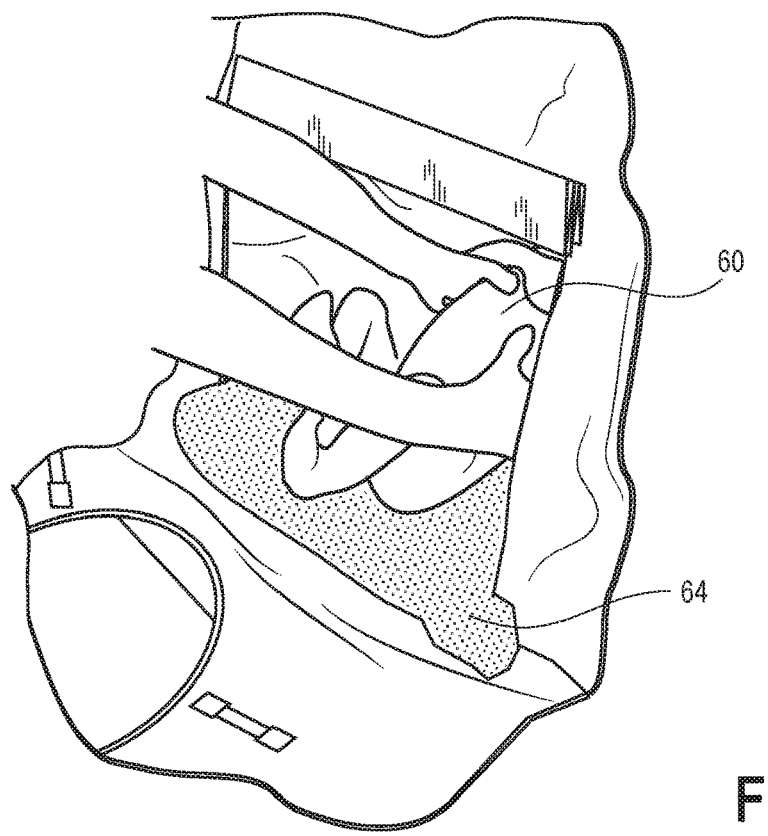
Figure 10E:
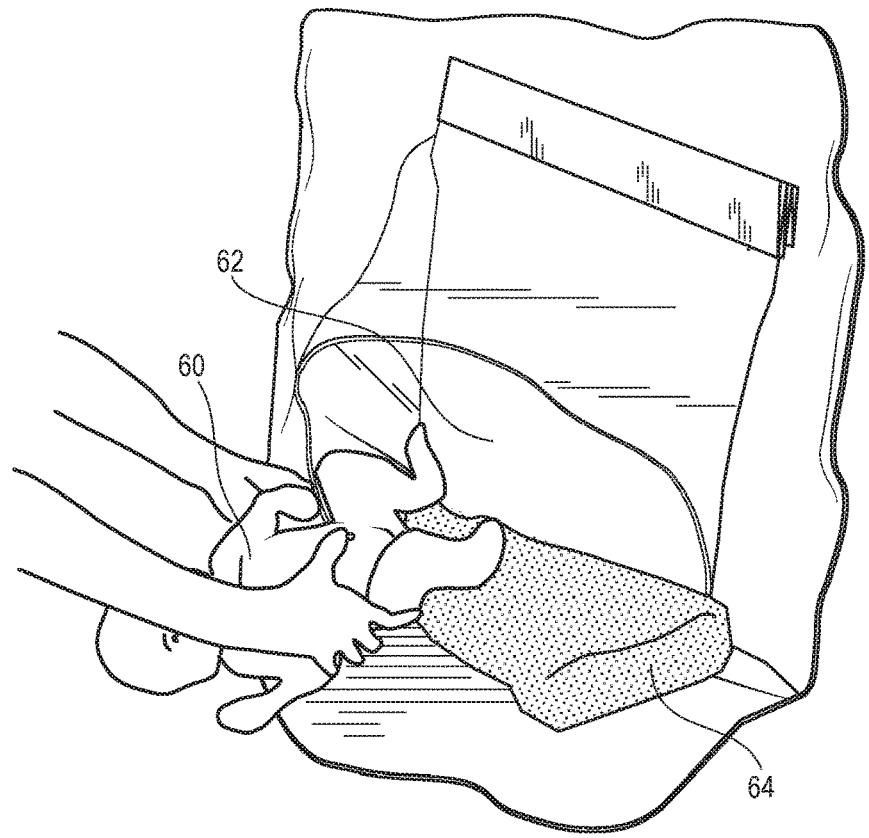

With reference now to FIG. 8, the surgeon-side flap 45 is provided to cover the screen fenestration 49. The flap 45 is secured to the screen 22 via tape 48 (FIG. 3) at the bottom and sides of the surgeon-side flap 45, and via a permanent adhesive connection near the top of the surgeon-side flap 45. Upon birth of the infant, or when birth is imminent, a caregiver may lift the surgeon-side flap 45 and fold the flap in an accordion-like manner via pre-folded accordion folds 56. The tape 48 at the bottom of the surgeon-side flap 45 may be used to secure this flap in the open position, as shown in FIG. 9. Thereafter, as shown in FIGS. 10A-E the infant 60 may be passed through the screen fenestration 49, and through the tunnel 62 that was formed by tearing open the tunnel structure, to then greet the mother. A sterile pad or blanket 64 may be placed over the patient to further enhance sterility.

Figure 11:
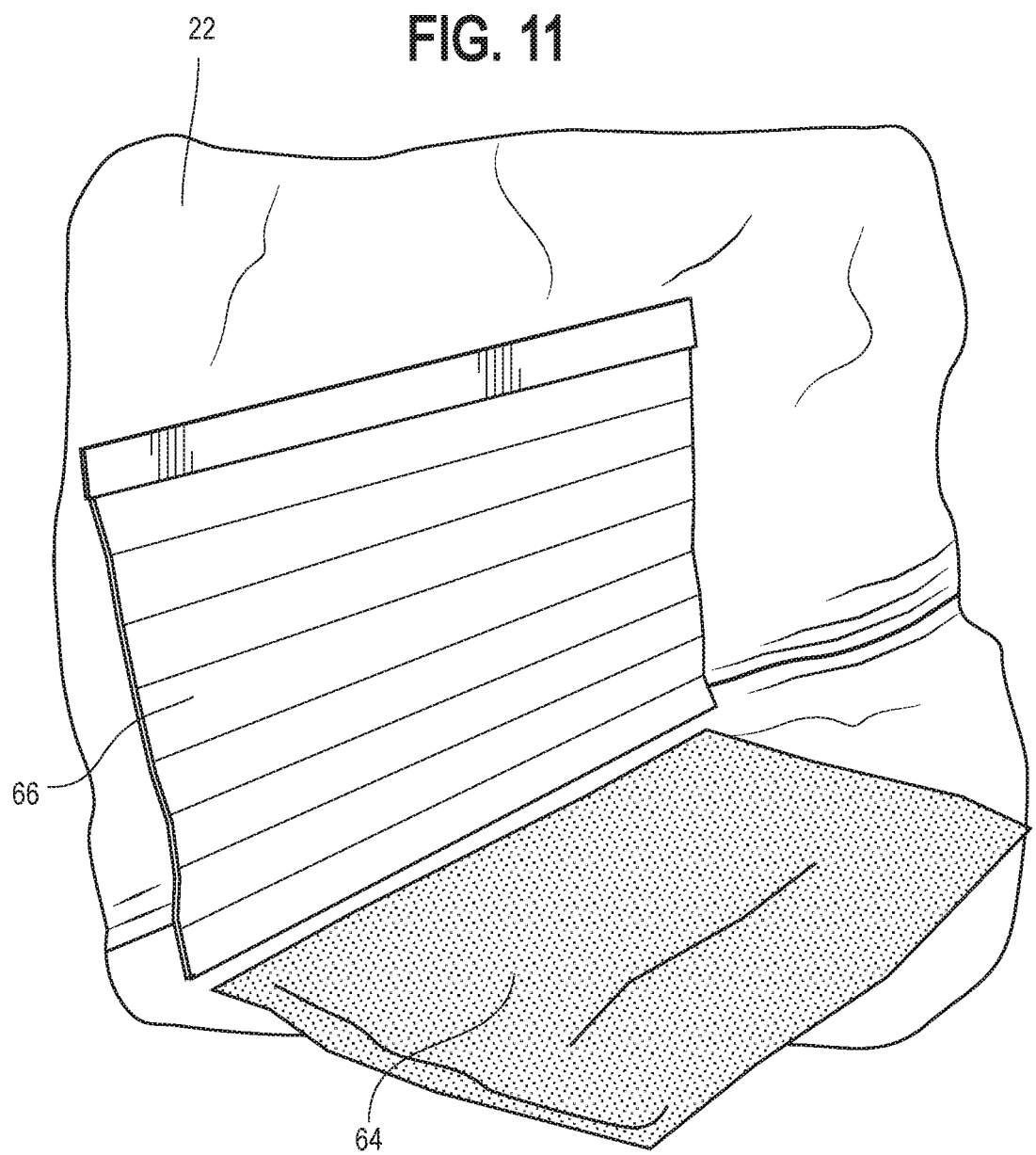
FIG. 11 is a perspective view of the drape taken from the patient-facing side of the screen after passage of the infant through the tunnel and after the patient-side flap has been secured in a closed position.

As shown in FIG. 11, the screen 22 is further provided with a patient-side flap 66. This patient-side flap 66 may be similarly connected to the screen via adhesive and via double-sided tape. The patient-side flap 66 generally will be secured in an open position until the infant is passed through the tunnel 62. At that point, the patient-side flap 66 may be moved and secured via tape into a closed position to cover the screen fenestration 49 to prevent the patient from viewing subsequent stages of the operation. The remainder of the C-section procedure may then be performed with the patient's vision in the direction towards the surgical site occluded by at least the patient-side flap 66. For purposes of antisepsis, the surgeon-side flap 45 (not shown in FIG. 11) also may be returned to the closed position to inhibit contamination of the surgical field. Generally, because the Cesarean section procedure is an invasive operation, it is highly desirable that the surgical side of the drape remain as sterile as possible to protect the surgical field. The patient side invariably cannot remain as sterile. The tunnel is believed to assist in protecting the sterility of the surgical field when passing an infant through the screen fenestration 49.

As supplied, the surgical drape 20 is initially provided in a sterile folded state wrapped in a sterile fabric wrapper (not shown) and an outer package (also not shown), as is conventional. The sterile fabric wrapper surrounds the surgical drape 20 to protect the surgical drape 20 and to maintain its sterile state. The wrapped surgical drape then is enclosed in a plastic pouch, which further protects the surgical drape and maintains its sterile condition.

The mainsheet and screen and armboard covers may be constructed of any suitable material, and as shown are constructed of a multi-layer combination of spunbond and meltblown materials as well as impervious films, commonly referred to as SMS nonwoven fabric, or bilaminated and trilaminated impervious and absorbent materials. The tunnel material is preferably composed of a clear or translucent plastic film material, such as a polyethylene film. Other parts of the drape may be composed of conventional materials.

It is thus seen that a drape that allows the surgeon to selectively permit the patient to view the area near the surgical field is provided. Via the above-described configuration, the mother is immediately able to bond with the infant and to greet the infant immediately after birth, while minimizing the risk of contamination to the surgical field. The drape enables the mother and the newborn infant to establish immediate skin-to-skin contact.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A surgical drape comprising:
a mainsheet having a mainsheet fenestration therein permitting access to a surgical region for performance of a surgical procedure when the drape covers a patient during the surgical procedure, the mainsheet having a head-oriented edge and having a surgeon-side and a patient-side;
a screen connected to the mainsheet at the head-oriented edge, the screen having a patient side and a surgeon side and having a screen fenestration, said screen further comprising tunnel wall portions formed of a flexible tunnel material that surround the screen fenestration, wherein the tunnel wall portions include a patient-facing wall portion and a bottom wall portion, the tunnel wall portions configured to extend away from the patient side of the screen and form a tunnel between the tunnel wall portions that is sized to allow passage of an infant, the screen further comprising at least one flap configured to inhibit a patient's visual access through the screen fenestration, wherein the at least one flap including a flap is attached to the screen on the patient side thereof.

2. A surgical drape according to claim 1, at least one flap including a second flap disposed on the surgeon side thereof.

3. A surgical drape according to claim 2, the second flap disposed on the surgeon side being originally in a closed position inhibiting visual access through the screen fenestration and the flap on the patient side being originally supplied in an open position not inhibiting the patient's visual access through the screen fenestration.

4. A surgical drape according to claim 1, further comprising a fluid collection pouch at least partially surrounding the mainsheet fenestration.

5. A method of performing surgery, comprising:
applying the surgical drape of claim 1 to a patient;
performing a Caesarean section operation on the patient and removing an infant from the patient;
with said at least one flap in an open position, passing the infant through the tunnel from the surgeon-side of the screen to the patient-side of the screen; and
closing at least one flap to inhibit visual access through the screen fenestration.

6. The method according to claim 5, including opening a first, surgeon-side flap, passing said infant through said tunnel, and closing the flap disposed on the patient side.

7. A surgical drape according to claim 1 wherein in an infant-receiving configuration, the tunnel wall portions extend from the patient side of the screen generally toward the patient.

8. A surgical drape according to claim 1 wherein the tunnel wall portions are formed of a clear or translucent material.

9. A surgical drape according to claim 1 wherein the tunnel wall portions include a sidewall that extends between the screen and the patient-facing wall portion.

10. A surgical drape according to claim 9 wherein a lower region of the sidewall extends a greater distance from the screen than an upper region of the sidewall.

11. A surgical drape according to claim 10 wherein the sidewall has a generally triangular configuration.

12. A surgical drape according to claim 1 wherein the patient-facing wall portion that is secured to the screen proximate the screen fenestration such that the patient-facing wall portion hangs downwardly across the screen fenestration.

13. A surgical drape according to claim 1 wherein the patient-facing wall portion is releasably secured to the bottom wall portion for allowing passage of the infant therebetween.

14. A surgical drape according to claim 1 further including perforations in the flexible tunnel material for separating adjacent tunnel wall portions for allowing passage of the infant between the separated adjacent tunnel wall portions.

15. The method according to claim 5 further comprising separating the patient-facing wall portion from the bottom wall portion to allow passage of the infant.

16. The method according to claim 15 wherein the separating includes tearing a perforation that releasable connects the patient-facing wall portion and the bottom wall portion.

17. The method according to claim 6 further comprising closing the first, surgeon-side flap such that flexible tunnel material is disposed between the first, surgeon-side flap and the flap disposed on the patient side.

18. A surgical drape comprising:
- a mainsheet having a mainsheet fenestration therein permitting access to a surgical region for performance of a surgical procedure when the drape covers a patient during the surgical procedure, the mainsheet having a head-oriented edge and having a surgeon-side and a patient-side;
- a screen connected to the mainsheet at the head-oriented edge, the screen having a patient side and a surgeon side and having a screen fenestration, said screen further comprising tunnel wall portions formed of a flexible tunnel material, the tunnel wall portions configured to extend away from the screen and form a tunnel between the tunnel wall portions that is sized to allow passage of an infant, the screen further comprising a patient-side flap and a surgeon-side flap configured to inhibit a patient's visual access through the screen fenestration, the flexible tunnel material including a patient-facing wall portion and a bottom wall portion that is releasably connected to the patient-facing wall portion for allowing passage of the infant therebetween, wherein the flexible tunnel material includes at least one perforation that releasably connects the patient-facing wall portion and the bottom wall portion.

19. The surgical drape according to claim 18 wherein the flexible tunnel material is disposed between the patient-side flap and the surgeon-side flap when the patient-side flap and the surgeon-side flap are in raised positions.

20. A surgical drape according to claim 1 wherein the flap is movable relative to the bottom wall.

* * * * *